US012685830B2

(12) United States Patent
Chow et al.

(10) Patent No.: US 12,685,830 B2
(45) Date of Patent: Jul. 21, 2026

(54) MEDICAL GAS DUCTS FOR MEDICAL GAS EVACUATION DEVICES AND RELATED SYSTEMS AND METHODS

(71) Applicant: INTUITIVE SURGICAL OPERATIONS, INC., Sunnyvale, CA (US)

(72) Inventors: Humphrey W. Chow, Cupertino, CA (US); Adam Klett, Mountain View, CA (US); Daryl Oshatz, Mountain View, CA (US); John W. Zabinski, Berkeley, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 571 days.

(21) Appl. No.: 18/254,674

(22) PCT Filed: Nov. 29, 2021

(86) PCT No.: PCT/US2021/060981
§ 371 (c)(1),
(2) Date: May 26, 2023

(87) PCT Pub. No.: WO2022/115686
PCT Pub. Date: Jun. 2, 2022

(65) Prior Publication Data
US 2024/0299677 A1 Sep. 12, 2024

Related U.S. Application Data

(60) Provisional application No. 63/119,048, filed on Nov. 30, 2020.

(51) Int. Cl.
*A61M 13/00* (2006.01)
*A61M 1/00* (2006.01)

(52) U.S. Cl.
CPC ............ *A61M 13/003* (2013.01); *A61M 1/79* (2021.05); *A61M 1/87* (2021.05); *A61M 2205/7545* (2013.01)

(58) Field of Classification Search
CPC ........ A61B 2218/008; A61B 2218/007; A61B 2218/00
See application file for complete search history.

(56) References Cited

U.S. PATENT DOCUMENTS 7,955,318 B1 6/2011 Schultz et al.
8,852,208 B2 10/2014 Gomez et al.
(Continued)

FOREIGN PATENT DOCUMENTS

CN 103781375 A 5/2014
CN 104287893 A 1/2015
(Continued)

OTHER PUBLICATIONS

International Search Report and Written Opinion for Application No. PCT/US2021/060981, mailed Mar. 21, 2022, 13 pages.

*Primary Examiner* — Deanna K Hall
(74) *Attorney, Agent, or Firm* — Jones Burke, PLLC

(57) ABSTRACT

A medical system can include a medical gas duct comprising a first end, a second end opposite the first end, a first opening at the first end of the duct, and a second opening at the second end of the duct. The first opening can be positioned to receive medical gas exiting an exhaust port of a medical gas evacuation unit. On the condition a medical suction supply provides a suction at the second opening of the duct, medical gas exiting the exhaust port of the medical gas evacuation unit flows into the first opening of the duct. Devices, systems, and methods relate to evacuating medical gasses.

17 Claims, 5 Drawing Sheets

(56)  References Cited

U.S. PATENT DOCUMENTS

| | | | |
|---|---|---|---|
| 9,295,524 | B2 | 3/2016 | Schena et al. |
| 9,358,074 | B2 | 6/2016 | Schena et al. |
| 2009/0221963 | A1 | 9/2009 | Lloyd et al. |
| 2017/0281255 | A1 | 10/2017 | Babini et al. |
| 2019/0159826 | A1 | 5/2019 | Horner et al. |
| 2020/0054799 | A1 | 2/2020 | Wang |
| 2020/0238025 | A1 | 7/2020 | Tang et al. |

FOREIGN PATENT DOCUMENTS

| | | |
|---|---|---|
| CN | 206656613 U | 11/2017 |
| CN | 108348661 A | 7/2018 |
| CN | 110072582 A | 7/2019 |
| CN | 111494031 A | 8/2020 |
| TW | 202029989 A | 8/2020 |

514

524

542

714

724

742

743

MEDICAL GAS DUCTS FOR MEDICAL GAS EVACUATION DEVICES AND RELATED SYSTEMS AND METHODS

CROSS-REFERENCE TO RELATED APPLICATION

This application is a U.S. national stage application under 35 U.S.C. § 371(c) of International PCT Application No. PCT/US2021/060981, filed Nov. 29, 2021 which claims the benefit of priority to U.S. Provisional Application No. 63/119,048, filed Nov. 30, 2020 titled "MEDICAL GAS DUCTS FOR MEDICAL GAS EVACUATION DEVICES AND RELATED SYSTEMS AND METHODS," the entire contents of each of which are incorporated by reference herein.

TECHNICAL FIELD

Aspects of the present disclosure relate to devices, systems, and methods for collecting and venting medical gas from a patient. Such gasses can include, for example, electrosurgical smoke particles and associated fumes resulting from electrocautery or electrosurgical procedures such as cutting, coagulating, and fulgurating tissue, or other medical and/or therapeutic gasses.

INTRODUCTION

Surgical procedures, such as laparoscopic surgery, can include electrocautery procedures and electrosurgical procedures such as cutting, coagulating, cauterizing, desiccating, and/or fulgurating tissue or other biological materials. Typically, during such surgical procedures, a surgical cavity is insufflated with an inert gas such as carbon dioxide to inflate the cavity and create workroom for the surgical procedure and provide an inert environment for the surgical procedure. The insufflation gas may be delivered, for example, through a cannula providing instrument access to the surgical cavity or via another device such as a Veress needle.

Byproducts such as smoke and other particulates and gasses may be generated during electrocautery and/or electrosurgical processes. Generally, such byproducts of the processes are cleared from the surgical cavity by a flow of gas that results from a pressure differential between the surgical cavity and the surrounding environment. The pressure differential can be generated solely by application of insufflation gas to the surgical cavity at a positive pressure relative to surrounding environment. Alternatively or additionally, a pressure differential between the surgical cavity and surrounding environment can be generated by application of negative relative pressure to the surgical cavity. The negative pressure can be supplied through another cannula providing access to the surgical cavity and can be generated by, for example, a medical gas evacuation unit including a vacuum pump. The medical gas evacuation unit can be or include, for example, an electrosurgical smoke evacuation system. The vacuum pump can be integral with the insufflator device or can be provided as a separate smoke removal system. The byproducts are typically vented from the vacuum pump to the surrounding ambient atmosphere, such as an operating room in which the procedure is being carried out. Some evacuation arrangements may include a filter configured to remove a portion of the particulate matter from the medical gas, but such filters may not effectively remove smaller particulates, including carcinogenic compounds and other chemicals. Additionally, filters may not fully filter fumes from the medical gas, so that the exhaust from the surgical cavity may contain harmful gaseous constituents that may or may not be detectable by smell.

Application of a second vacuum source, such as a medical vacuum typically available in hospital operating rooms, directly to the exhaust port of the medical gas evacuation unit's vacuum pump could overwhelm the unit's vacuum pump or otherwise negatively influence the device. And in addition, this second vacuum source could overwhelm the insufflator's ability to supply insufflation gas and so cause the insufflated body cavity to collapse. Thus, complex gas pressure and flow volume control and metering of the medical vacuum based on varying operational states of the unit's vacuum pump and insufflator would be required to prevent overwhelming the unit's vacuum pump and collapsing the surgical cavity or otherwise negatively influence the device.

A need exists to remove medical gas from the surgical site without exhausting the gas (filtered or unfiltered) to the operating room environment and without adding burdensome complexity and control requirements to the evacuation/insufflation system unit or to the secondary vacuum system outside the unit.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one aspect of the present disclosure, a medical system comprises a medical gas duct comprising a first end, a second end opposite the first end, a first opening at the first end of the duct, and a second opening at the second end of the duct. The first opening is positioned to receive medical gas exiting an exhaust port of a medical gas evacuation unit. On a condition a medical suction supply provides a suction at the second opening of the duct, medical gas exiting the exhaust port of the medical gas evacuation unit flows into the first opening of the duct.

In accordance with at least another aspect of the present disclosure, a system for exhausting gas used in a medical procedure, comprises a medical gas evacuation unit. The medical gas evacuation unit comprises a tube configured to receive gas from a body cavity of a patient, a vacuum source operably coupled to the tube, a particulate filter positioned to filter gas received from the tube, and an exhaust port positioned to vent gas received from the tube out of the medical gas evacuation unit. The system further includes a duct comprising an inlet and an outlet. The outlet is configured to be removably coupled to a vacuum source, and the inlet is positioned relative to the exhaust port to enable a suction force through the duct to draw gas away from the exhaust port and into the duct.

In accordance with yet another aspect of the present disclosure, a method of exhausting a gas from a patient comprises receiving, at a medical gas evacuation unit, gas from a body cavity of a patient, wherein the body cavity surrounds a site of a medical procedure, exhausting the medical gas received at the medical gas evacuation unit from the medical gas evacuation unit to an ambient environment external to the medical gas evacuation unit, and drawing the medical gas exhausting from the medical gas evacuation unit into a duct.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure and are incorporated in and constitute a part of this specification. The drawings illustrate one or more embodiments of the present teachings and together with the description explain certain principles and operation. In the drawings.

DETAILED DESCRIPTION

Figure 1:
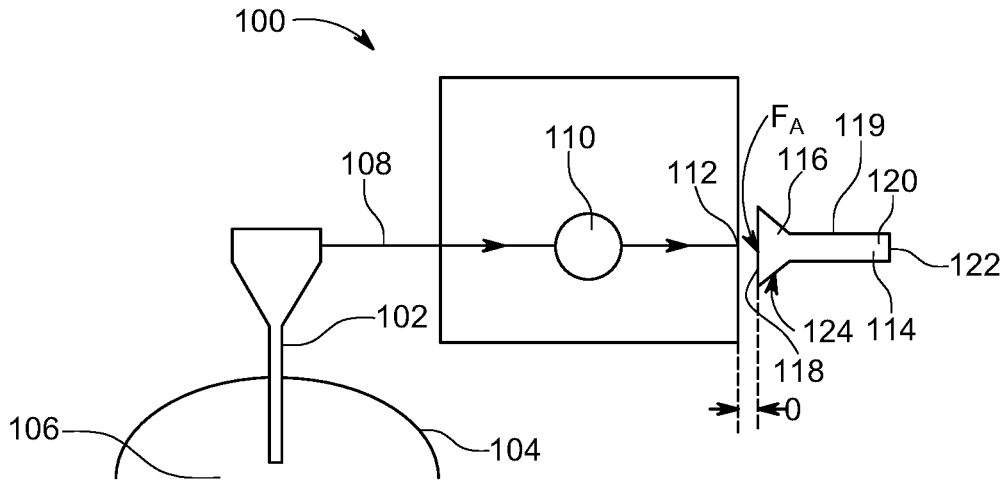
FIG. 1 is a schematic view of a cannula, vacuum pump, and medical gas duct according to an exemplary embodiment of the present disclosure.

The present disclosure relates to evacuating medical gasses associated with a surgical procedure, such as an electrosurgical procedure, from a surgical environment without negatively impacting an insufflation pressure present at a surgical site. Further, the present disclosure provides a system for clearing medical gasses from a surgical site and operating room environment using a vacuum source readily available in surgical environments, such as a centrally plumbed medical suction supply as used in many hospital and operating room environments.

Such sources of vacuum, such as a medical suction supply, cannot always be applied directly to an exhaust port of an insufflator, because the negative pressure and resulting flow rate of these systems is too great and would evacuate insufflation gas from the surgical site too quickly and cause collapse of the cavity. Flow controls such as a regulator valve or fixed orifice could be used with the medical suction supply to reduce the flow rate. However, the exhaust does not flow constantly from the exhaust port, because the insufflation flow rate can vary based on a number of possible circumstances surrounding the maintenance of the surgical cavity such as leaks or action of an electrosurgical tool, action of a smoke evacuator, or other conditions. For example, the insufflation flow rate can be increased during action of the electrosurgical tool to assist in clearing smoke and other byproducts from the surgical cavity. Thus, even if flow controls such as a regulator or orifice were used with the medical suction supply, this approach would still result in inconsistent insufflation pressure and inconsistent inflation of the surgical cavity. Further, constant monitoring and control of the level of vacuum directly applied to exhaust port would require a complex control system calibrated with and in communication with the insufflation system and associated instruments. Such controls would introduce an undesirable level of complexity in the insufflation system.

Devices in accordance with the present disclosure are configured such that a constant source of vacuum, such as that provided by a central suction supply in a hospital or clinic environment, can be used to evacuate medical gasses without the precise and constant monitoring and adjustment that would be required if such a vacuum source were to be applied directly to the exhaust port of the insufflator device.

According to the present disclosure, a medical gas duct can include a hood with a first opening at a first end and a second opening at a second end, the second opening being configured to be operably coupled to a source of vacuum. The first opening can be positioned adjacent to an exhaust port of a medical gas evacuation device, such as a vacuum pump that may be associated with a standalone medical gas evacuation device or a medical gas evacuation device integral with an insufflation device. The second opening can be coupled to a vacuum source, such as a central vacuum system plumbed to the operating room or other area in which the surgical procedure is carried out. The first opening can be positioned such that it is exposed to an ambient environment (e.g., air in the operating room) surrounding the insufflator device. Coupling of the vacuum source to the duct and applying vacuum to the second opening results in a flow of air into the first opening, out through the second opening, and into the vacuum source. The medical gas is entrained into the flow of air, and the gasses and particulates in the exhaust can be filtered and/or otherwise processed by, e.g., a central vacuum supply system.

The hood can optionally be spaced far enough away from the exhaust port such that the vacuum source is not applied directly to the exhaust port, but close enough that any medical gasses leaving the exhaust port are entrained in a flow of ambient air from the surrounding environment. Thus, the vacuum source can be operating constantly without negatively affecting the insufflation pressure in the surgical cavity. In this way, the present disclosure prevents medical gasses leaving the insufflation device from diffusing in the operating room or other surrounding environment, and does not require a complex control system in communication with the insufflation device.

Figure 2:
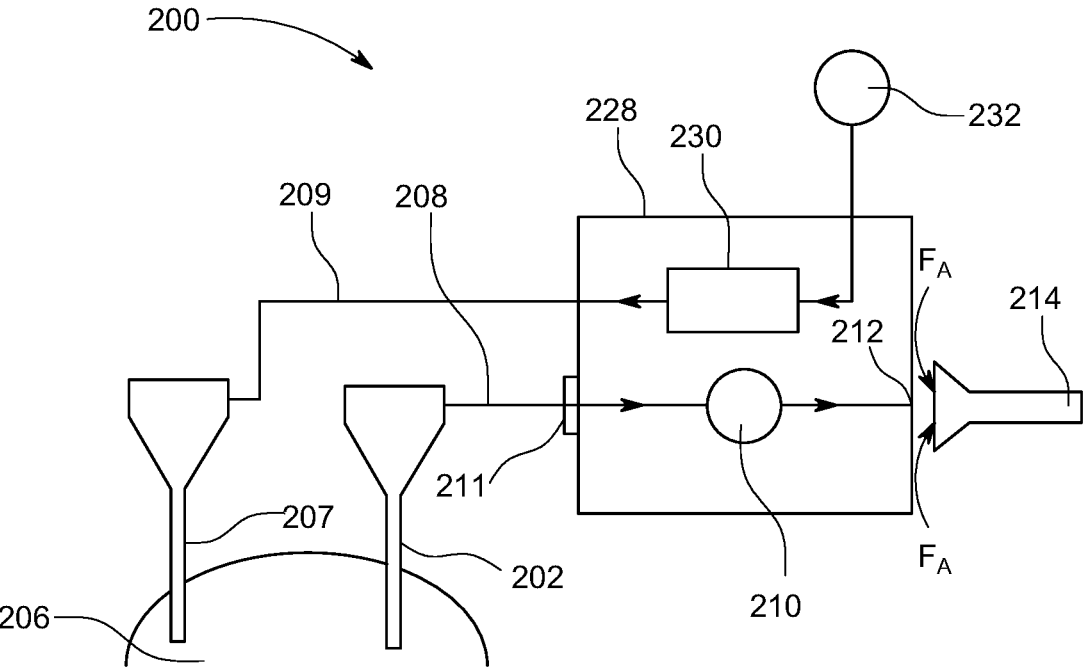
FIG. 2 is a schematic view of an insufflation device including a vacuum pump and a medical gas duct according to an exemplary embodiment of the present disclosure.

Referring now to FIG. 1, a schematic view of an embodiment of a medical gas evacuation system 100 according to the present disclosure is shown. In the exemplary system of FIG. 1, a cannula 102 extends through a body wall 104 of a patient to provide access to a surgical site 106. The surgical site 106 may be a body cavity and may optionally be inflated with an insufflation gas as further discussed in connection with FIG. 2 below. The cannula 102 may be used to provide access to the surgical site 106 for one or more surgical instruments, such as an electrosurgical or electrocautery instrument, a mechanical instrument such as forceps, clip applier, needle driver, or any other instrument. Additionally, the surgical instrument(s) can be or include an imaging instrument such as an endoscope, camera, etc.

Various surgical procedures can be carried out by inserting a surgical instrument through the cannula 102 to obtain access to the surgical site 106. For some procedures, multiple instruments may be used by inserting them concurrently or in turn through the cannula 102, through one or more additional cannulas, through other surgical access devices such as ports, or any combination thereof. During a surgical procedure involving electrocautery or electrosurgical processes, process byproducts such as smoke and other particulates, fumes, odors, and other byproducts can be generated. Such byproducts can include, but are not limited to, carcinogens and other compounds, and can potentially contaminate the surgical site, obscure view through an imaging device, or have other undesirable effects. Accordingly, the cannula 102 is coupled via a tube 108 or other conduit to a medical gas evacuation unit such as vacuum pump 110, which is configured to apply a negative pressure through the tube 108 and cannula 102 to the surgical site 106. The negative pressure applied by the vacuum pump 110 removes medical gasses (e.g., smoke and other byproducts of the surgical procedure) from the surgical cavity. The medical gasses leave the vacuum pump 110 via an exhaust port 112.

In conventional systems, the exhaust port 112 is configured to exhaust the gasses directly to the ambient air in the operating room or other environment in which the surgical procedure is being carried out, because the vacuum pump 110 must be carefully calibrated and controlled to remove the medical gasses without collapsing the surgical site 106. Any significant change to the pressure levels at the exhaust port 112, such as an increase in back pressure by connecting additional tubing or other conduit to the exhaust port 112, or applying a vacuum directly to the exhaust port 112, could impact the flow rate from the vacuum pump 110 to such a degree that either the vacuum pump 110 is unable to draw medical gasses from the surgical site quickly enough, or the gasses are drawn out so quickly that insufflated surgical site 106 collapses.

The present disclosure addresses this problem and provides a system that facilitates removal of the medical gasses from the exhaust port without permitting them to accumulate in the ambient environment and without introducing additional complication to the control and operation of the medical gas evacuation system 100. According to various embodiments of the disclosure, the medical gas evacuation system 100 includes a medical gas duct 114 with a first end portion 116 having a first opening 118 and a second end portion 120 with a second opening 122. The second opening 122 is configured to be fluidly coupled to a vacuum source, such as a medical suction supply (e.g., a centrally-located vacuum system plumbed to different locations in a hospital or clinic building) or another source of suction external to the insufflation device.

The first end portion 116 of the medical gas duct 114 comprises a hood portion 124 defining the first opening 118. The hood portion 124 (and thus the first opening 118) are positioned adjacent to the exhaust port 112, but the medical gas duct 114 remains open to the ambient air. For example, in the embodiment of FIG. 1, the hood portion 124 is adjacent to the exhaust port 112 but does not directly cover or completely occlude the exhaust port 112. Rather, as shown in FIG. 1, the hood portion 124 is spaced from the exhaust port 112 by a distance D, leaving the first opening 118 of the duct at least partially open to ambient air. The distance D may be on the order of millimeters, such as, for example, 1 millimeter, 5 millimeters, 10 millimeters, or more.

The hood portion 124 defines a cross-sectional area of the medical gas duct 114 at the first end portion 116 that is larger than a cross-sectional area of the medical gas duct 114 at the second end portion 120. A middle portion 119 of the duct can comprise a cross-sectional area similar in size to the second end portion 120 and thus smaller than the area of the first end portion 116 with the hood portion 124. Stated another way, the first end portion 116 flares outwardly from the middle portion 119 to the first opening 118. Alternatively, the medical gas duct 114 can taper gradually from the first end portion 116 through the middle portion 119 to the second end portion 120.

Suction applied to the second opening 122 of the medical gas duct 114 generates a flow through the medical gas duct 114. Air in the ambient environment is drawn into the medical gas duct 114 through the space (defined by the distance D) between the exhaust port 112 and the hood portion 124. Flow of ambient air in FIG. 1 into the first opening 118 of the medical gas duct 114 is indicated by $F_A$. Because ambient air is free to flow into the medical gas duct 114, the suction applied at the second opening 122 of the medical gas duct 114 can be relatively large in magnitude and continuous without creating a pressure differential large enough to significantly alter operation of the vacuum pump 110 nor to collapse the insufflated surgical site 106.

During a surgical procedure in which surgical medical gasses are produced, the medical gas duct 114 can be coupled to a suction source to generate flow of ambient air $F_A$. Medical gasses removed from the surgical site 106 by the vacuum pump 110 and released at the exhaust port 112 are entrained within the flow $F_A$ and collected by a central vacuum system, thereby removing the medical gasses from the operating room environment.

In some exemplary embodiments of the disclosure, the vacuum pump 110 is contained within an insufflation device, and the insufflation device provides both insufflation gas and evacuates byproducts of surgical procedures from the surgical site. For example, referring now to FIG. 2, a system 200 includes an insufflation device 228 including a vacuum pump 210 and an insufflation gas control system 230. The insufflation gas control system 230 meters flow from a source of insufflation gas 232 (e.g., a portable gas cylinder or a central gas supply) through the insufflation device 228, into a first cannula 207 via tube 209 or other conduit, and into the surgical site 206 to inflate the surgical site 206. The insufflation device 228 can be referred to as a surgical insufflation gas supply system.

The vacuum pump 210 is connected to a second cannula 202 via tube 208 or other conduit in an arrangement similar to that discussed above in connection with FIG. 1. The insufflation gas control system 230 and the vacuum pump 210 can be controlled together by an electronic control system (not shown) that correlates evacuation of the surgical site via the vacuum pump 210 and delivery of insufflation gas via the insufflation gas control system 230. For example, during electrosurgical or electrocautery operations, the vacuum pump 210 may operate to clear particulates and fumes from the surgical site 206 while the insufflation gas control system 230 delivers a flow volume of insufflation gas sufficient to maintain inflation of the surgical site 206.

Operation of the vacuum pump 210 is as discussed above in connection with FIG. 1, and the system 200 includes a medical gas duct 214, similar to medical gas duct 114 discussed in connection with FIG. 1, configured to draw medical gas from an exhaust port 212 through which medical gas leaves the vacuum pump 210. The medical gas from the exhaust port 212 is entrained within a flow of ambient air $F_A$ that flows into the medical gas duct 214 between the medical gas duct 214 and the insufflation device 228. Instruments used in carrying out the surgical procedure can be inserted within cannulas 202 and 207, and/or other cannulas or access locations, to access the surgical site 206. In some exemplary embodiments, the tubes 208 and 209 can be provided as an integral tube set with a single connector assembly configured to couple the tubes 208 and 209 to the insufflation device 228 simultaneously. The integral tube set can also include a particulate filter 211 configured to at least partially filter the medical gas exiting the tube 208 to the vacuum pump 210. The filter 211 can be located in a gas flow path between a gas inlet port to which the tube 208 is coupled and the exhaust port 212.

Optionally, the insufflation device 228 can be contained within an equipment rack, such as, for example, a side cart that includes other equipment supporting a surgical procedure, such as power supply, electronic controls related to displays and other ancillary equipment, gas cylinders for the insufflation gas supply, and other components. In such an embodiment, the insufflation device and medical gas duct are located inside such a cart and may be covered by a housing, side panels, etc.

Figure 3:
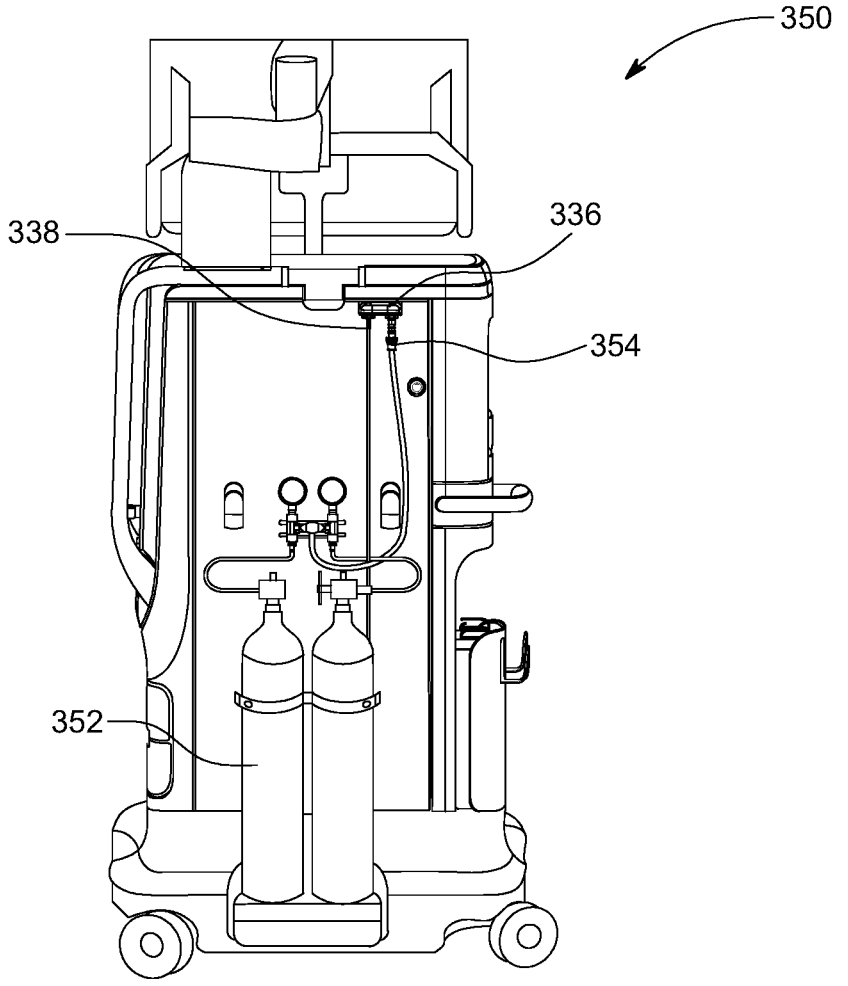
FIG. 3 is a side view of a side cart according to the present disclosure.

Referring now to FIG. 3, a side view of an exemplary embodiment of a side cart 350 of a surgical system is shown. The side cart can be configured for supporting surgical procedures, such as teleoperated surgical procedures including electrosurgical or electrocautery procedures. The side cart 350 can be configured to be used in conjunction with, for example, a patient side cart comprising manipulators for actuating surgical instruments and a surgeon console comprising controls and viewing devices for operating the patient side cart. Embodiments described herein may be used, for example, with remotely operated, computer-assisted systems (such as, for example, teleoperated surgical systems) such as those described in, for example, U.S. Pat. No. 9,358,074 (filed May 31, 2013) to Schena et al., entitled "Multi-Port Surgical Robotic System Architecture", U.S. Pat. No. 9,295,524 (filed May 31, 2013) to Schena et al., entitled "Redundant Axis and Degree of Freedom for Hardware-Constrained Remote Center Robotic Manipulator", and U.S. Pat. No. 8,852,208 (filed Aug. 12, 2010) to Gomez et al., entitled "Surgical System Instrument Mounting", each of which is hereby incorporated by reference in its entirety. Further, embodiments described herein may be used, for example, with teleoperated surgical systems that operate at least in part with computer assistance, such as the da Vinci® Surgical System, the da Vinci Si® Surgical System, the da Vinci X® Surgical System, the da Vinci Xi® Surgical System, or the da Vinci SP® Surgical System, all commercialized by Intuitive Surgical, Inc., of Sunnyvale, California.

The side cart 350 can include a source of insufflation gas, such as gas cylinders 352. The gas cylinders 352 can provide a supply of pressurized inert gas, such as carbon dioxide, to inflate the surgical site. In other embodiments, the source of insufflation gas may be a hose or tube coupled to a central source of pressurized gas, such as a building-wide (e.g., hospital-wide) source. Additionally, other chemically and biologically inert gasses can be used, such as helium, medical air, therapeutic gasses, or other gasses.

The side cart 350 includes a manifold 336 with a gas inlet 354 to which the source of insufflation gas can be fluidly coupled, e.g., by a hose or other conduit. The gas inlet on the manifold 336 is in turn fluidly coupled to an insufflation device (e.g., insufflation device 228 in FIG. 2 or insufflation device 428 in FIG. 4) which may be an integral or removable component of the side cart 350 that delivers insufflation gas to the surgical site, as discussed in further detail above in connection with FIG. 2.

The manifold 336 also comprises a medical suction supply connector, such as suction port 338 to which a source of vacuum can be coupled. The source of vacuum can be, e.g., a central vacuum source plumbed to a room in which the surgical procedure is carried out. Alternatively, the source of vacuum can be a separate vacuum device, such as a portable vacuum source or other device. The source of vacuum can be plumbed to the suction port 338 with a hose, pipe, or other conduit. As a non-limiting example, the source of vacuum can be a central medical suction system. The suction system configured to deliver vacuum at, for example, in a range of from 300 to 500 mmHg below atmospheric pressure. In some situations, the suction port 338 can be connected to a source of vacuum via a pressure regulator and/or a line splitter (e.g., Y-fitting) device. For example, some operating room environments may have access to only a single vacuum line. Use of vacuum may be necessary for other purposes, such as for a suction irrigator, in addition to the use for evacuation of exhaust gases, and a configuration including Y-fittings and/or pressure regulators can enable use of a single line vacuum source for multiple purposes.

Figure 4:
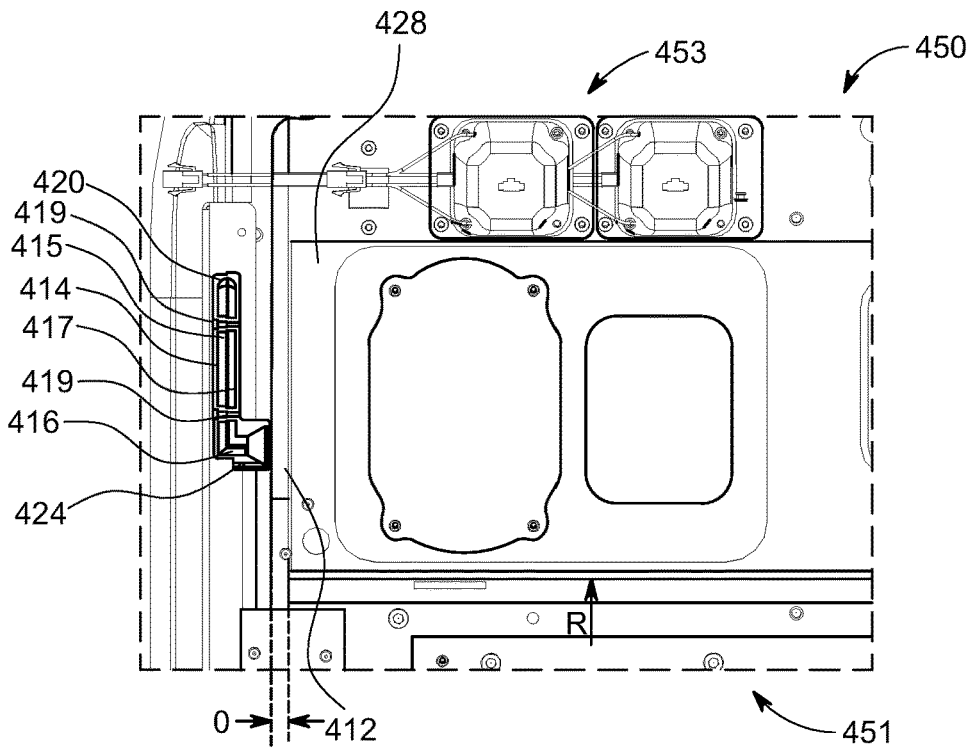
FIG. 4 is cross-sectional top view of a side cart including an insufflation device and a medical gas duct according to an exemplary embodiment of the present disclosure.

Referring now to FIG. 4, a top view of an insufflation device 428 is shown inside a side cart 450. The insufflation device 428 has an exhaust port 412 in fluid communication with a vacuum pump (not shown) internal to the insufflation device 428 and similar to vacuum pumps 110 and 210 discussed in connection with FIGS. 1 and 2. A medical gas duct 414 is coupled to the side cart 450 such that a hood portion 424 at a first end 416 of the medical gas duct 414 is located adjacent to the exhaust port 412. The medical gas duct 414 has a second end 420 configured to be removably coupled to a suction source, such as, for example, a tube or conduit coupled to a centrally located medical suction system.

As shown in FIG. 4, the hood portion 424 of the medical gas duct 414 is positioned adjacent to, but not directly covering or fully occluding, the exhaust port 412. In the specific embodiment of FIG. 4, a distance D from the exhaust port 412 to the hood portion 424 of the medical gas duct may be, for example, approximately 10 millimeters. Distances D of less than or greater than 10 millimeters are within the scope of the disclosure. The appropriateness of such different distances may depend on, among other factors, the relative sizes of the exhaust port 412 and the hood portion 424, the negative pressure of the external suction supply and the flow rate generated thereby, flow rate from the exhaust port, a shape of an inner wall of the hood portion 424, direction of the exhaust stream, amount of turbulence in the exhaust stream, turbulence in the ambient environment, turbulence within the hood, and other factors.

The insufflation device 428 can be configured for routine removal from and insertion into the side cart 450 for maintenance and/or replacement of the insufflation device 428. For example, in the embodiment of FIG. 4, the insufflation device 428 is inserted into the side cart 450 in a direction R. That is, the insufflation device 428 is installed in the side cart 450 by sliding the insufflation device 428 into the side cart 450 in the direction R, which may be, for example, from a rear side 451 of the side cart 450 toward a front side 453 of the side cart 450. Accordingly, the exhaust port 412 is positioned on a side of the insufflation device 428 that is parallel to direction R so that the medical gas duct 414 does not interfere with removal and replacement of the insufflation device 428. Stated another way, the medical gas duct can be placed on a lateral surface of the insufflation device 428 that is parallel to the direction R of movement of the insufflation device 428 for removal of the insufflation device 428 from the side cart 450. Other arrangements and locations of the exhaust port 412 are within the scope of the disclosure, such as the exhaust port 412 being positioned on any side or surface of the insufflation device 428, including, for example and not limitation, any side of the insufflation device 428 out of the path of removal of the insufflation device 428 from the side cart 450.

As shown in FIG. 4, the medical gas duct 414 can comprise two separate components to facilitate manufacturing of the medical gas duct 414. For example, the medical gas duct 414 can comprise first and second components 415 and 417, respectively. The first and second components 415 and 417 may comprise a polymer material and may be configured for ease of manufacturing, such as by injection molding or other forming processes. The first and second components 415 and 417 may be configured to include integral features configured to couple the first and second components 415 and 417 to one another to form the medical gas duct 414. For example, in the embodiment of FIG. 4, the first and second components 415 and 417 comprise snap fit features 419 that couple the first and second components 415 and 417 together. In other embodiments, the medical gas duct 414 can comprise a single component, more than two components configured to be coupled to one another, or other configurations. Further, while the medical gas duct 414 of FIG. 4 comprises a polymer material, other materials, such as composite materials, metal and metal alloys, and other materials are considered within the scope of the present disclosure.

The medical gas duct 414 can comprise a constant internal cross-sectional shape along the length of the medical gas duct 414, such as an oval cross section, a generally square cross section, a rectangular cross section, or other cross-sectional shapes, without limitation. Further, the internal cross-sectional shape of the medical gas duct 414 can vary along the length of the medical gas duct 414. As discussed in connection with FIG. 6 below, portions of the medical gas duct 414, such as the hood portion 424, can comprise a hyperbolic cross-sectional shape that can optionally transition to other cross-sectional shapes in the middle portion and second end portion of the medical gas duct 414.

Figure 5:
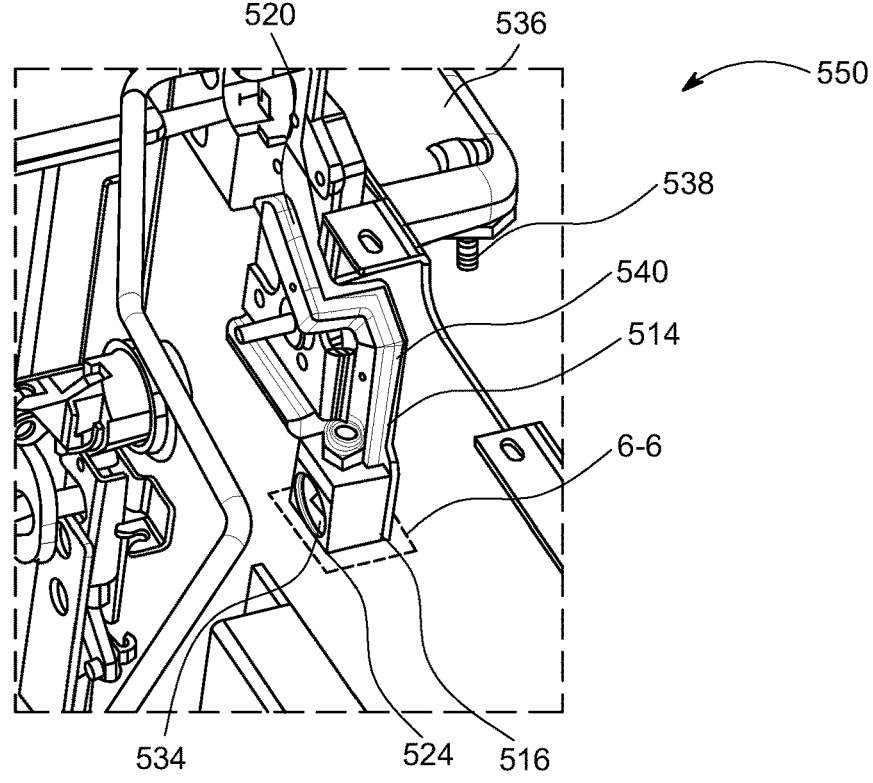
FIG. 5 is a partial perspective view of a medical gas duct and manifold of a side cart according to an exemplary embodiment of the disclosure.

Referring now to FIG. 5, a partial perspective view of a medical gas duct 514 is shown. The medical gas duct 514 is shown in situ within a cart 550 with the insufflation device omitted to better illustrate the medical gas duct 514. The medical gas duct 514 comprises a general shape configured to accommodate the features and configuration of the cart 550. For example, the medical gas duct 514 can be configured with a middle portion 540 that extends from a second end 520 in fluid communication with a manifold 536 to a first end 516 with a hood portion 524 having an inlet aperture 534 positioned to be adjacent an exhaust port of an insufflation device, such as exhaust port 412 (FIG. 4) of insufflation device 428 (FIG. 4). The middle portion 540 and end portions 516, 520 can have various shapes and arrangements based on the desired location and packaging of the manifold and insufflation device (e.g., insufflation device 428 in FIG. 4) relative to the overall arrangement of the cart 550.

The manifold 536 can include a suction port 538 to which a source of suction can be attached. The source of suction can be, e.g., a hose or other conduit operably coupled to a source of medical vacuum, such as a central vacuum system, or a stand-alone vacuum pump or other device. The suction port 538 can comprise, for example, a barbed hose fitting as shown in FIG. 5 or other suitable fittings such as a flare fitting, pipe fitting, luer fitting, etc.

The hood portion 524 and inlet aperture 534 can be configured to facilitate flow of ambient air into the medical gas duct 514. For example, the hood portion 524 can have an inner wall with a particular cross-sectional shape that supports the flow of ambient air into the inlet aperture and entrainment of any medical gas that exits the exhaust port (e.g., exhaust port 412 in FIG. 4) into the flow of ambient air.

Figure 6:
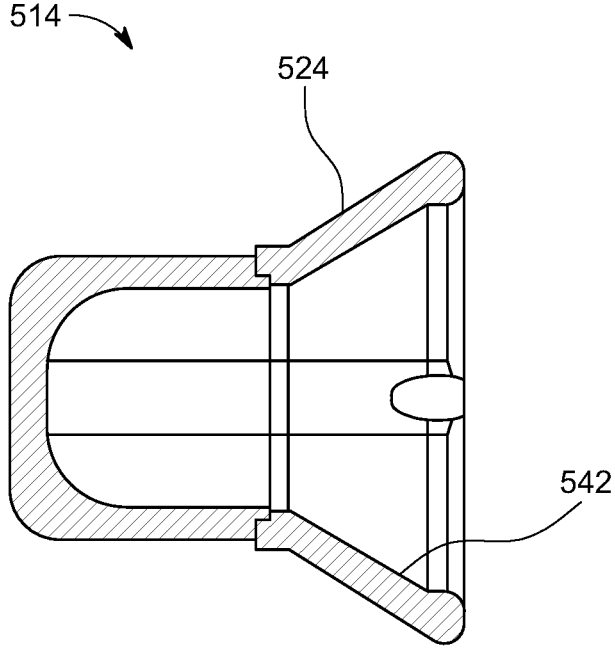
FIG. 6 is a cross-sectional view of an inlet aperture of a medical gas duct according to the present disclosure.
Figure 7:
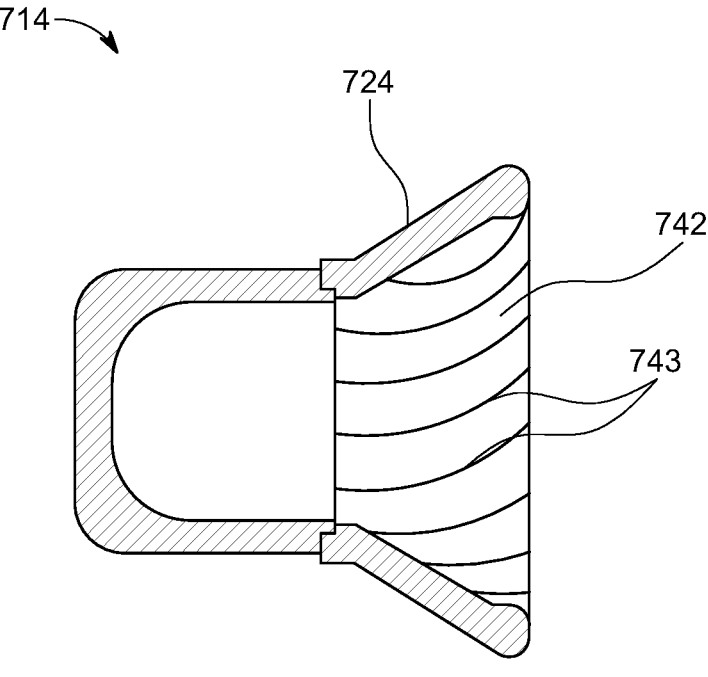
FIG. 7 is a cross-sectional view of an inlet aperture of a medical gas duct according to another aspect of the present disclosure.

Referring now to FIG. 6, a cross-sectional view taken at line 6-6 of FIG. 5, the hood portion 524 and inlet aperture 534 of the medical gas duct 514 of FIG. 5 are shown in cross section. The cross section reveals the shape of an inner wall 542 of the hood portion 524, which, in FIG. 6, comprises a hyperbolic shape. The hyperbolic shape of the inner wall 542 can facilitate flow of ambient air and medical gas into the hood portion 524 by, e.g., promoting a generally laminar flow profile of the ambient air and medical gas. The hyperbolic shape is provided as an example only, and other shapes, such as conical, pyramidal, tetrahedral, or other shapes, without limitation, are within the scope of the present disclosure. Additionally or alternatively, the inner wall 542 of the hood portion 524 can include other shapes and/or features to promote laminar flow, such as, for example, flutes configured to generate a vortex within the hood portion 524. Further, edges of the hood portion 524 can be radiused, chamfered, or otherwise relieved to promote laminar flow. For example, referring now to FIG. 7, a hood portion 724 of a medical gas duct 714 includes an inner wall 742 comprising a plurality of flutes 743. The plurality of flutes 743 can be configured to generate a vortex in the hood portion 724, which may further contribute to laminar flow and promote collection of medical gas within a flow of ambient air through the hood portion 724. While various features are discussed herein as promoting laminar flow, actual flow characteristics of the medical gas ducts disclosed herein can include laminar flow, transitional flow, and turbulent flow. Further, flow characteristics can vary along the length of the medical gas duct, such as varying between laminar, transitional, and turbulent flow.

Figure 8:
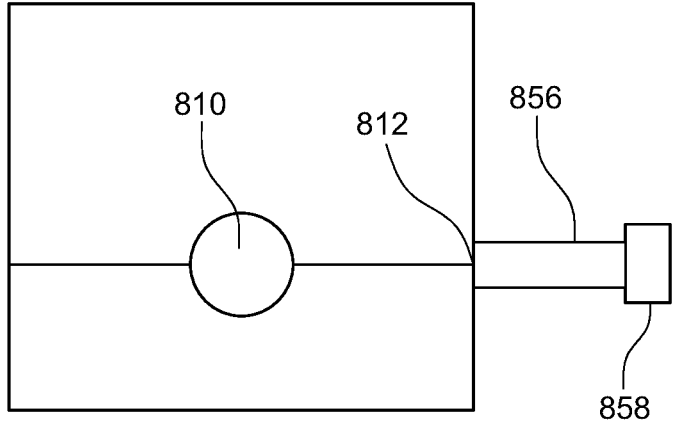
FIG. 8 is a schematic view of a medical gas evacuation unit with a medical gas duct according to another exemplary embodiment of the present disclosure.

According to the embodiments of FIGS. 1, 2, 4, and 5 above, the medical gas duct 114, 214, 414 is spaced from the exhaust port 112, 212, 412 by a gap of distance D such that a flow of ambient air is drawn into the medical gas duct 114, 214, 414 with the flow of medical gas. In other embodiments, the medical gas duct may be placed directly over the exhaust port. For example, referring now to FIG. 8, a medical gas duct 856 is located directly over the exhaust port 812 of a vacuum pump 810. In this embodiment, the suction applied by the medical gas duct 856 (e.g., by a central suction source or other device connected to a second end of the medical gas duct as described in detail in connection with FIGS. 2 and 5 herein) may be regulated passively or actively by a pressure regulator 858 that regulates the amount of suction applied to exhaust port 812 by the medical gas duct 856. The pressure regulator 858 can optionally be calibrated such that a suction applied directly to the exhaust port 812 by the medical gas duct 856 generates a flow at a rate and/or volume insufficient to collapse the insufflated surgical site, but sufficient to draw medical gasses away from the exhaust port 812. Alternatively, the pressure regulator 858 can be configured to actively regulate the flow such that suction is only applied when necessary to clear byprod- ucts from the surgical site (e.g., surgical site 106 (FIG. 1) or 206 (FIG. 2) based on control information from the insuf- flation device (e.g., insufflation device 228 in FIG. 2) relating to the rate of insufflation gas entering the surgical site, operation of a surgical instrument, and other control information.

Figure 9:
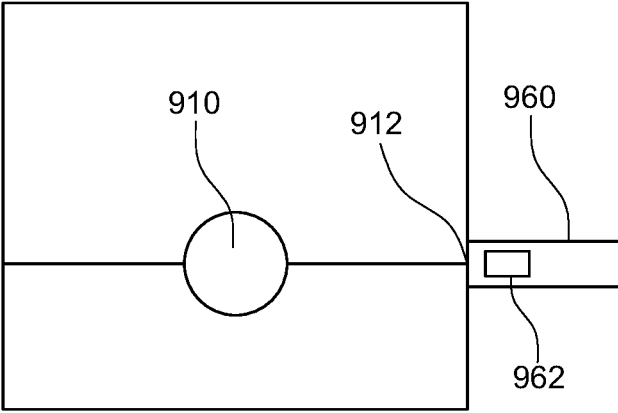
FIG. 9 is a schematic view of a medical gas evacuation unit with a medical gas duct according to yet another exemplary embodiment of the present disclosure.

Further, in some embodiments, the medical gas duct may be positioned directly over the exhaust port and the medical gas duct itself may comprise features to ensure the level of suction applied through the medical gas duct is insufficient to collapse the insufflated surgical site. For example, refer- ring now to FIG. 9, a medical gas duct 960 is directly over the exhaust port 912 of a vacuum pump 910, but is none- theless open to a flow of ambient air through one or more apertures 962 formed in the medical gas duct 960. The apertures 962 function in a manner similar to the spacing between the medical gas duct and exhaust port as discussed in connection with FIGS. 1, 2, 4, and 5, in that a continuous flow of ambient air enters the duct 960 as a result of suction applied to the medical gas duct 960, and any medical gas leaving the vacuum pump 910 is entrained within the flow of air removed from the operating environment.

Embodiments according to the present disclosure provide robust and reliable devices and methods for removing objec- tionable surgical medical gasses from an operating environ- ment. Many of these exemplary embodiments do not have any requirement for a control system in communication with an insufflation device to control flow rate, and instead can operate independently of the insufflation device.

The embodiments described herein are not limited to the systems noted above, and various other teleoperated, com- puter-assisted surgical system configurations may be used with the embodiments described herein. Various embodi- ments described herein can optionally be used in conjunc- tion with hand-held, manual instruments.

This description and the accompanying drawings that illustrate various embodiments should not be taken as lim- iting. Various mechanical, compositional, structural, electri- cal, and operational changes may be made without departing from the scope of this description and the invention as claimed, including equivalents. In some instances, well- known structures and techniques have not been shown or described in detail so as not to obscure the disclosure. Like numbers in two or more figures represent the same or similar elements. Furthermore, elements and their associated fea- tures that are described in detail with reference to one embodiment may, whenever practical, be included in other embodiments in which they are not specifically shown or described. For example, if an element is described in detail with reference to one embodiment and is not described with reference to another embodiment, the element may never- theless be claimed as included in the other embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the invention. For example, spatially relative terms— such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exem- plary term "below" can encompass both positions and orientations of above and below. A device may be otherwise oriented (rotated 90 degrees or at other orientations) and the spatially relative descriptors used herein interpreted accord- ingly.

Further modifications and alternative embodiments will be apparent to those of ordinary skill in the art in view of the disclosure herein. For example, the devices and methods may include additional components or steps that were omit- ted from the diagrams and description for clarity of opera- tion. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifi- cations to structure, dimensions, materials, and methodolo- gies may be made without departing from the scope of the present teachings.

Other embodiments in accordance with the present dis- closure will be apparent to those skilled in the art from consideration of the specification and practice of the inven- tion disclosed herein. It is intended that the specification and examples be considered as exemplary only, with the follow- ing claims being entitled to their fullest breadth, including equivalents, under the applicable law.

What is claimed is:

1. A medical system comprising:

a medical gas duct comprising a first end, a second end opposite the first end, a first opening at the first end of the duct, and a second opening at the second end of the duct;

wherein the first opening is positioned to receive medical gas exiting an exhaust port of a medical gas evacuation unit with a gap between the first end of the duct and the medical gas evacuation unit; and wherein in a state of a medical suction supply providing suction at the second opening of the duct, medical gas exiting the exhaust port of the medical gas evacuation unit flows into the first opening of the duct and ambient environmental air flows through the gap between the first end of the duct and the medical gas evacuation unit and into the first opening of the duct.

2. The medical system of claim 1, wherein:

the duct comprises a middle portion and a first end portion that extends from the middle portion of the duct to the first end of the duct;

the first end portion of the duct comprises the first opening of the duct; and a cross-sectional area of the first opening of the duct is larger than a cross-sectional area of the middle portion of the duct.

3. The medical system of claim 2, wherein:

the first end portion flares outward from the middle portion of the duct to the first end of the duct.

4. The medical system of claim 2, wherein:

the first end portion of the duct comprises an inner wall; and a shape of the inner wall along an axial cross section of the first end portion is hyperbolic.

5. The medical system of claim 2, wherein:

the first end portion of the duct comprises an inner wall; and the inner wall comprises a plurality of flutes.

6. The medical system of claim 1, wherein:

the medical system further comprises a medical suction supply connector at the second end of the duct.

7. The medical system of claim 6, wherein:

the medical system further comprises the medical suction supply; and the medical suction supply is operably coupled to the medical suction supply connector.

8. The medical system of claim 1, wherein:

the medical system further comprises the medical gas evacuation unit;

the medical gas evacuation unit comprises an electrosurgical smoke evacuation system; and the electrosurgical smoke evacuation system comprises a gas inlet port, the exhaust port of the medical gas evacuation unit, and a particulate filter in a gas flow path between the gas inlet port and the exhaust port of the medical gas evacuation unit.

9. The medical system of claim 1, wherein:

the medical system further comprises the medical gas evacuation unit; and the medical gas evacuation unit comprises a surgical insufflation gas supply system.

10. The medical system of claim 1, wherein:

the medical system further comprises the medical gas evacuation unit and an equipment rack configured to support the medical gas evacuation unit;

the medical gas evacuation unit comprises a lateral surface, and the medical gas evacuation unit is insertable into the equipment rack along the lateral surface; and the exhaust port of the medical gas evacuation unit is located on the lateral surface of the medical gas evacuation unit.

11. The medical system of claim 10, wherein:

the first opening of the medical gas duct is elongate along an axis parallel to a direction of insertion of the medical gas evacuation unit into the equipment rack.

12. A system for exhausting gas used in a medical procedure, the system comprising:

a medical gas evacuation unit and a duct;

a tube configured to receive gas from a body cavity of a patient, wherein the medical gas evacuation unit comprises:

a first vacuum source operably coupled to the tube, a particulate filter positioned to filter gas received from the tube, and an exhaust port positioned to vent gas received from the tube out of the medical gas evacuation unit; and wherein the duct comprises:

an outlet configured to be removably coupled to a second vacuum source external to the medical gas evacuation unit, and an inlet positioned with a gap between the inlet and the exhaust port of the medical gas evacuation unit, wherein in a state of the outlet operably coupled to the second vacuum source, suction force through the duct draws gas away from the exhaust port and into the duct and ambient environmental air flows through the gap between the inlet of the duct and the medical gas evacuation unit and into the inlet of the duct.

13. The system of claim 12, wherein:

a shape of the inlet of the duct is configured to promote laminar flow of ambient environmental air flow entering the inlet of the duct.

14. The system of claim 12, wherein:

a shape of the inlet of the duct is configured to promote laminar flow of gas from the exhaust port of the medical gas evacuation unit into the inlet of the duct.

15. The system of claim 12, wherein:

the medical gas evacuation unit comprises a surgical insufflation gas supply system.

16. The system of claim 12, wherein:

the inlet of the duct comprises an inner wall; and a shape of the inner wall along an axial cross section of the inlet is hyperbolic.

17. A method of exhausting a gas from a patient, the method comprising:

receiving, at a medical gas evacuation unit, gas from a body cavity of a patient in which a site of a medical procedure is located;

exhausting the gas received at the medical gas evacuation unit from the body cavity through an exhaust port of the medical gas evacuation unit to an ambient environment external to the medical gas evacuation unit; and drawing, via medical suction supplied to a medical gas duct, the gas exhausting from the exhaust port of the medical gas evacuation unit into the medical gas duct through an opening spaced via a gap from the exhaust port,

wherein during the drawing of the gas exhausting from the exhaust port of the medical gas evacuation unit, ambient environmental air flows into the opening of the medical gas duct through the gap.

* * * * *